US008431904B2

(12) United States Patent  (10) Patent No.: US 8,431,904 B2
Lewellen et al.  (45) Date of Patent: Apr. 30, 2013

(54) DATA-PROCESSING ELECTRONICS FOR USE IN A POSITRON-EMISSION TOMOGRAPHY SYSTEM

(75) Inventors: Thomas K. Lewellen, Port Ludlow, WA (US); Robert S. Miyaoka, Shoreline, WA (US)

(73) Assignee: University of Washington, Seattle, WA (US)

( * ) Notice: Subject to any disclaimer, the term of this patent is extended or adjusted under 35 U.S.C. 154(b) by 135 days.

(21) Appl. No.: 13/125,962

(22) PCT Filed: Oct. 26, 2009

(86) PCT No.: PCT/US2009/062108
§ 371 (c)(1),
(2), (4) Date: May 24, 2011

(87) PCT Pub. No.: WO2010/048626
PCT Pub. Date: Apr. 29, 2010

(65) Prior Publication Data
US 2011/0215248 A1  Sep. 8, 2011

Related U.S. Application Data (60) Provisional application No. 61/108,439, filed on Oct. 24, 2008.

(51) Int. Cl.
*G01T 1/164* (2006.01)
(52) U.S. Cl.
USPC ............ 250/363.03; 250/363.04; 250/363.02; 250/362

(58) Field of Classification Search .............. 250/363.03
See application file for complete search history.

(56) References Cited

U.S. PATENT DOCUMENTS

| 7,227,149 B2* | 6/2007 | Stearns et al. | 250/363.03 |
| 7,528,375 B2* | 5/2009 | Matsumoto | 250/370.01 |
| 2003/0105397 A1 | 6/2003 | Turner | |
| 2004/0188623 A1 | 9/2004 | Breeding | |
| 2006/0186341 A1* | 8/2006 | Ueno et al. | 250/363.05 |
| 2007/0051893 A1* | 3/2007 | Matsumoto | 250/370.01 |

OTHER PUBLICATIONS

International Search Report mailed Jun. 3, 2010, issued in corresponding International Application No. PCT/US2009/062108, filed Oct. 26, 2009, 1 page.
Lewellen, T.K., et al., "Design of a Second Generation Firewire Based Data Acquisition System for Small Animal PET Scanners," IEEE Nuclear Science Symposium Conference Record (1997), Oct. 2008, pp. 5023-5028.

* cited by examiner

*Primary Examiner* — David Porta
*Assistant Examiner* — Djura Malevic
(74) *Attorney, Agent, or Firm* — Christensen O'Connor Johnson Kindness PLLC (57) ABSTRACT

Improved processing electronic hardware are disclosed that facilitate the efficient processing of PET system data, while enhancing accuracy and compatibility of PET systems with other analytical methods (e.g., magnetic resonance imaging). Improvements include the use of an application-specific integrated circuit (ASIC) for summing, by row, column, and diagonal, the output signals from an array of photodetectors in the PET system.

17 Claims, 7 Drawing Sheets

DATA-PROCESSING ELECTRONICS FOR USE IN A POSITRON-EMISSION TOMOGRAPHY SYSTEM

CROSS-REFERENCE TO RELATED APPLICATION

This application claims the benefit of U.S. Provisional Application No. 61/108,439, filed Oct. 24, 2008, the disclosure of which is hereby expressly incorporated by reference in its entirety.

STATEMENT OF GOVERNMENT LICENSE RIGHTS

This invention was made with Government support under Contract Nos. EB002117, CA088194, and EB001563, both awarded by National Institute of Biomedical Imaging and BioEngineering (NIBIB). The Government has certain rights in the invention.

BACKGROUND

The ability to produce images of the inside of a living organism without invasive surgery has been a major advancement in medicine over the last one hundred years. Imaging techniques such as X-ray computed tomography (CT) and magnetic resonance imaging (MRI) have given doctors and scientists the ability to view high-resolution images of anatomical structures inside the body. While this has led to advancements in disease diagnosis and treatment, a large set of diseases causes changes in anatomical structure only in the late stages of the disease or never at all. This has given rise to a branch of medical imaging that captures certain metabolic activities inside a living body. Positron emission tomography (PET) is in this class of medical imaging.

Positron Emission Tomography

PET is a medical imaging modality that takes advantage of radioactive decay to measure certain metabolic activities inside living organisms. PET imaging systems comprise three main components, indicated schematically in FIG. 1, a radioactive tracer that is administered to the subject to be scanned, a scanner that is operable to detect the location of radioactive tracer (indirectly as discussed below), and a tomographic imaging processing system.

Figure 1:
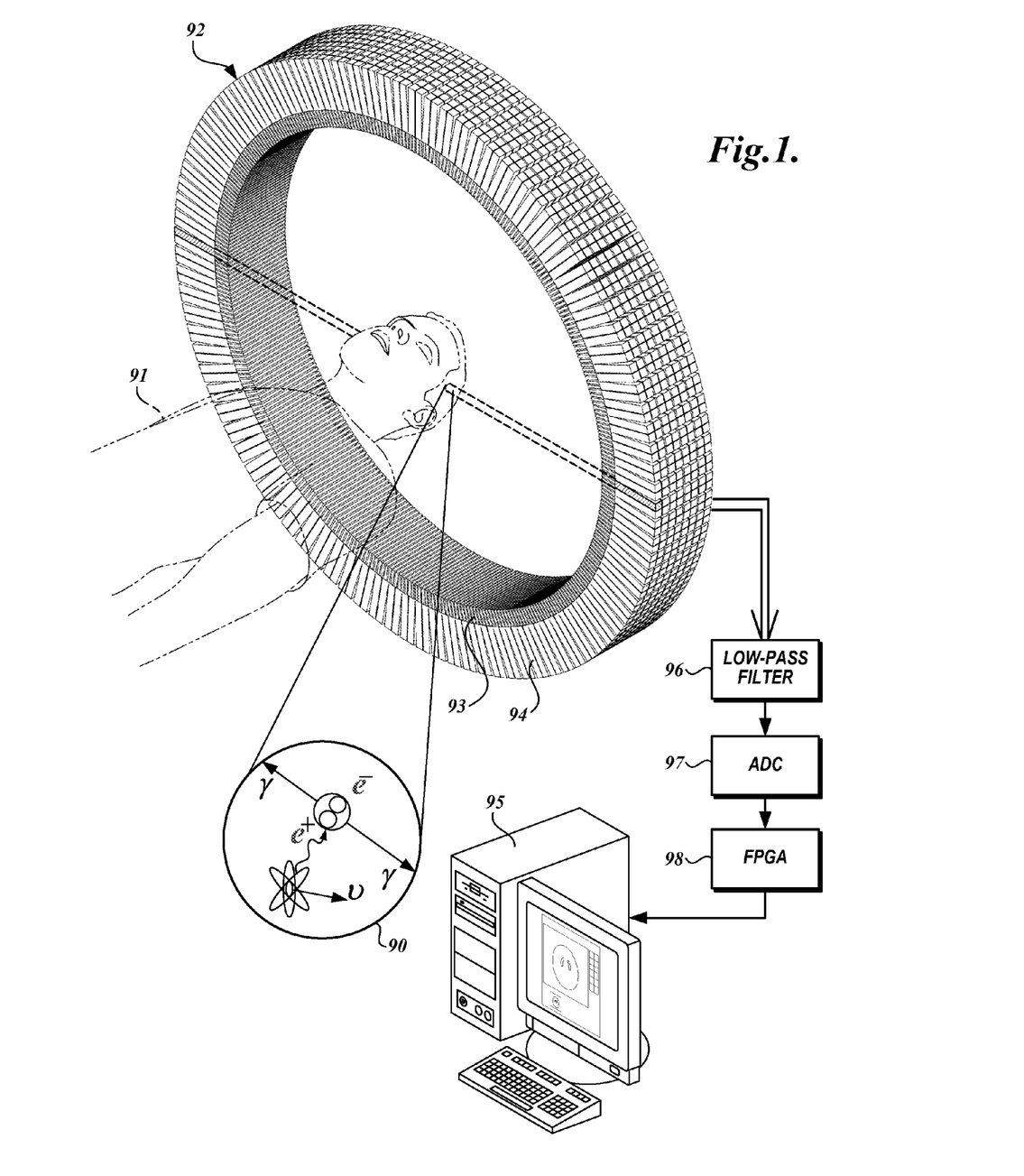
FIG. 1 is an environmental view showing a PET scanner system in accordance with the present invention.

The first step is to produce and administer a radioactive tracer 90, comprising a radioactive isotope and a metabolically active molecule. The tracer 90 is injected into the body to be scanned 91. After allowing time for the tracer 90 to concentrate in certain tissues, the body 91 is positioned inside the scanner 92. The radioactive decay event for tracers used in conventional PET studies is positron emission. Radioactive decay in the tracer 90 emits a positron $e^+$. The positron $e^+$ interacts with an electron $e^-$ in the body in an annihilation event that produces two 511 KeV anti-parallel photons or gamma photons γ. The scanner 92 detects at least some of the 511 KeV photons γ generated in the annihilation event.

The scanner 92 includes a ring of sensors and front-end electronics that process the signals generated by the sensors. The sensors typically comprise scintillator crystals or scintillators 93 and photodetectors 94 (e.g., photomultiplier tubes (PMT), silicon photomultipliers (SiMP) or avalanche photo diodes (APD)). The scintillator crystal 93 interacts with the 511 KeV gamma photons γ to produce many lower-energy photons, typically visible light photons. The photodetector 94 detects the visible light photons and generate a corresponding electrical pulse or signal. The electric pulses are processed by front-end electronics to determine the parameters or characteristics of the pulse (i.e., energy, timing). Unless the context implies otherwise, for convenience references to a photodetector herein will be understood to include any mechanism or device for detecting gamma photons such as 511 KeV photons and producing lower-energy photons such as visible light photons in response.

Finally, the data is sent to a host computer 95 that performs tomographic image reconstruction to turn the data into a 3-D image.

Radiopharmaceutical

To synthesize the tracer 90, a short-lived radioactive isotope is attached to a metabolically active molecule. The short half-life reduces the subject's exposure to ionizing radiation, but generally requires the tracer 90 be produced close to the scanner. The most commonly used tracer is fluorine-18 flourodeoxyglucose ([F-18]FDG), an analog of glucose that has a half-life of 110 minutes. [F-18]FDG is similar enough to glucose that it is phosphorylated by cells that utilize glucose, but does not undergo glycolysis. Thus, the radioactive portion of the molecule becomes trapped in the tissue. Cells that consume a lot of glucose, such as cancers and brain cells, accumulate more [F-18]FDG over time relative to other tissues.

After sufficient time has passed for the tissue of interest to uptake enough tracer 90, the scanner 92 is used to detect the radioactive decay events, i.e., by detecting the 511 KeV photons. When a positron is emitted, it typically travels a few millimeters in tissue before it annihilates with an electron, producing two 511 KeV photons directed at 180°±0.23° from one another.

Photon Scintillation

Most of the 511 KeV photons will pass through the body tissue (and other materials) without significant interaction. While this typically allows the photon to travel through and exit the body, the gamma photons are difficult to detect. Photon detection is the task of the scintillator 93. A scintillator 93 absorbs gamma photons and emits lower energy photons, typically visible light photons. A scintillator 93 can be made from various materials including plastics, organic and inorganic crystals, and organic liquids. Each type of scintillator has a different density, index of refraction, timing characteristics, and wavelength of maximum emission.

In general, the density of the scintillator crystal determines how well the material stops the gamma photons. The index of refraction of the scintillator crystal and the wavelength of the emitted light affect how easily light can be collected from the crystal. The wavelength of the emitted light also needs to be matched with the device that will turn the light into an electrical pulse (e.g., the photodetector) in order to optimize the efficiency. The scintillator timing characteristics determine how long it takes the visible light to reach its maximum output (rise time) and how long it takes to decay (decay time). The rise and decay times are important because the longer the sum of these two times, the lower the number of events a photodetector can handle in a given period, and thus the longer the scan will take to get the same number of counts. Also, the longer the timing characteristics, the greater the likelihood that two events will overlap (pile-up) and data will be lost.

The 511 KeV photons may undergo two types of interactions within the scintillator 93: Compton scattering, wherein the photon will lose energy and change direction, and photoelectric absorption. For example, a particular gamma photon may (i) experience photoelectric absorption in its first interaction in the scintillator crystal, (ii) undergo Compton scattering one or more times within the crystal prior to photoelectric absorption, or (iii) may undergo Compton scattering one or more times within the crystal before being ejected from the crystal.

Photodetectors

Attached to the scintillator 93 are electronic photodetectors 94 that convert the visible light photons from the scintillator 93 into electronic pulses. The two most commonly used devices are PMTs and APDs. A PMT is a vacuum tube with a photocathode, several dynodes, and an anode that has high gains to allow very low levels of light to be detected. An APD is a semiconductor version of the PMT. Another technology that is currently being studied for use in PET scanners are SiPMs. SiPMs (also called Geiger-Mode APDs (GM-APD)) comprise an array of semiconducting photodiodes that operate in Geiger mode so that when a photon interacts and generates a carrier, a short pulse of current is generated.

In an exemplary SiPM, the array of photodiodes comprises about 103 diodes per $mm^2$. All of the diodes are connected to a common silicon substrate so the output of the array is a sum of the output of all of the diodes. The output can therefore range from a minimum wherein one photodiode fires to a maximum wherein all of the photodiodes fire. This gives these devices a linear output even though they are made up of digital devices.

Image Construction

Referring to FIG. 1, a PET system acquires data as follows: photodetector 94 data is filtered with a low-pass filter 96, digitized with an analog to digital converter 97, and the digitized data is initially processed with field programmable gate arrays (FPGAs) 98.

The analog pulses generated by the photodetector 94 contain the information used to create a PET image. The analog pulses are processed to extract start time, location, and total energy. The apparatus for performing this initial processing is referred to as the front-end electronics, and includes the filters 96, ADCs 97, and FPGAs 98. The analog pulse received from the photodetector 94 is filtered with the low pass filter 96 to remove noise, and then digitized with the ADC 97, for processing by the FPGA 98. Another consideration is the number of inputs to the FPGA 98. Very fast ADCs have a parallel output which would require 10-12 bits per channel, with tens to hundreds of channels per FPGA. The number of inputs would thus outnumber the amount that even modern FPGAs can handle. Therefore, current systems use serial output ADCs 97, which limits the sampling rate to around 100 MSPS. However, for systems requiring fewer ADCs per FPGA, faster ADCs can be used to achieve better timing resolution.

After the analog pulse data is digitized, the requisite pulse parameters can be extracted in the FPGA 98. A total pulse energy, for example, may be obtained by summing the samples of the pulse values and subtracting out the baseline (the output value of the ADC 97 without an input pulse).

Finally, the data is sent to a host computer 95 that performs tomographic image reconstruction to turn the data into a 3-D image.

An important advantage of PET imaging is that the annihilation event produces two substantially anti-parallel 511 KeV photons. Therefore, with detectors disposed around the body being imaged, two detection events may be observed at roughly the same time (coincident events) in two oppositely-disposed sensors. The annihilation event producing the 511 KeV photons will be located somewhere on the line connecting the two photon detection points. The line connecting two coincident events is referred to as the line of response (LOR). When enough coincidental events have been detected, image reconstruction can begin. Essentially the detected events are separated into parallel lines of response (interpreted path of photon pair) that can be used to create a 3-D image using computer tomography. Methods for creating images using computer tomography are well known in the art. It will be appreciated that the accuracy of the 3-D PET images is dependent on the accuracy of the estimated LORs.

While PET, MRI, and CT are all common medical imaging techniques, the information obtained from the different modalities is quite different. MRI and CT give anatomical or structural information. That is, they produce a picture of the inside of the body. This is great for problems such as broken bones, torn ligaments or anything else that presents as abnormal structure. However, MRI and CT do not indicate metabolic activity. This is the domain of PET. The use of metabolically active tracers means that the images produced by PET provide functional or biochemical information.

Oncology (study of cancer) is currently the most common application of PET. Certain cancerous tissues metabolize more glucose than normal tissue. [F-18]FDG is close enough to glucose that cancerous cells readily absorb it and, therefore, they have high radioactive activity relative to background tissue during a scan. This enables a PET scan to detect some cancers before they are large enough to be seen on an MRI scan. PET scan information is also very useful for monitoring treatment progression as the quantity of tracer uptake can be tracked over the progression of the therapy. If a scan indicates lower activity in the same cancerous tissue after therapy, it indicates the therapy is working.

PET is also useful in neurology (study of the nervous system) and cardiology (study of the heart). An interesting application in neurology is the early diagnosis of Parkinson's disease. Tracers have been developed that concentrate in the cells in the brain that produce dopamine, a neurotransmitter. In patients with Parkinson's disease, neurons that produce dopamine reduce in number. Therefore, a scan of a Parkinson's patient would have less activity than a healthy patient's. This can lead to early diagnosis, since many of the other early signs of Parkinson's are similar to other diseases.

Detector Design

Figure 2:
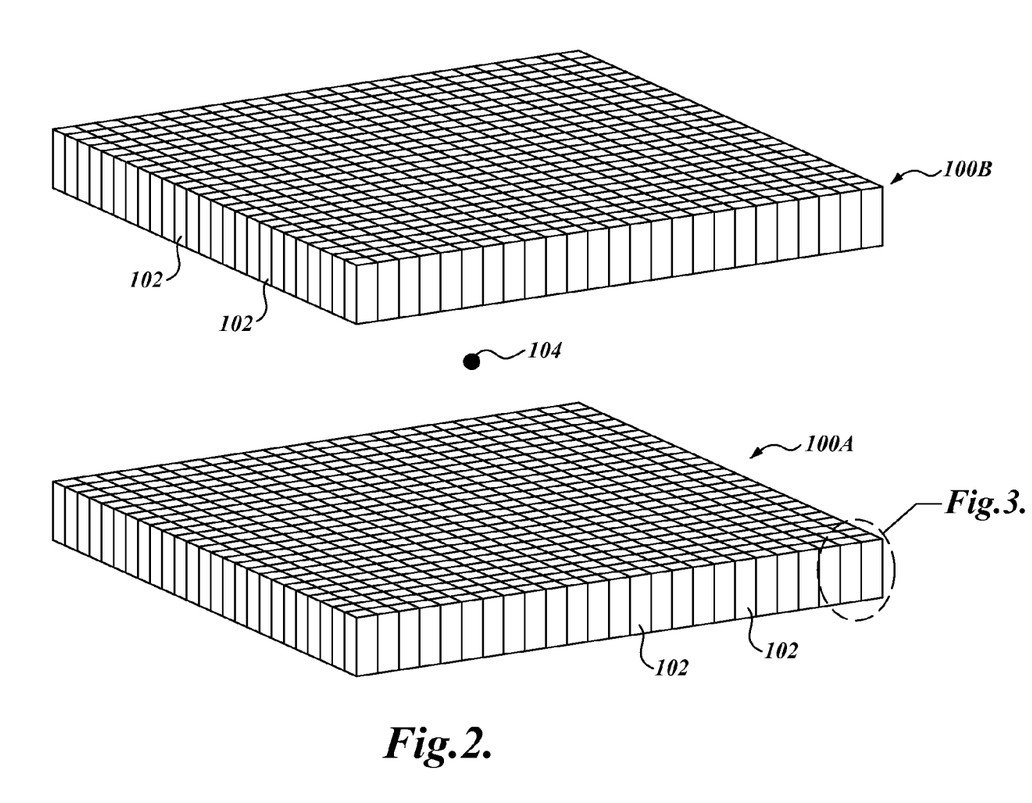
FIG. 2 shows schematically a pair of oppositely disposed detector modules.

In a typical PET scanner 92, detectors comprising scintillators 93 and photodetectors 94 are used to perform data acquisition for image construction. FIG. 2 illustrates schematically two opposed detector modules 100A and 100B, each module comprising an array of detector elements 102. Two common types of detector elements are the continuous miniature crystal element (cMiCe) and the discrete miniature crystal element (dMiCE). The cMiCe and dMiCE detectors operate using different scintillator configurations and, in some cases, hardware and software for processing detector data.

The cMiCe detector is a continuous crystal having photodetectors mounted on at least one surface of the crystal in a specific configuration (e.g., a grid array). Because scintillation events occur in continuous crystal, and photons produced by the scintillation may spread over an area greater than that of a single photodetector, photons may be detected by multiple detectors for a single event. The light is not contained, artificially (as in a dMiCE detectors), in an area above a detector, and, so, hardware and software must be provided in the PET system to capture, analyze, and process the received photon signals from the annihilation events so as to construct an image.

Figure 3:
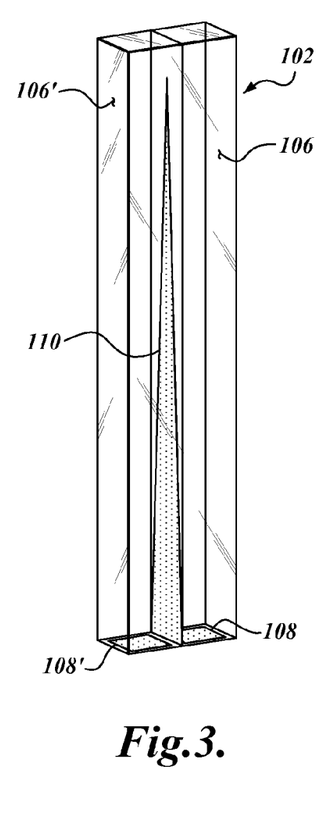
FIG. 3 shows an exemplary prior art dMiCE crystal pair detector element, suitable for use in the detector modules shown in FIG. 2.

The dMiCE detector modules have traditionally been used to achieve high spatial resolution for small-animal PET scanners. A dMiCE crystal pair detector element 102 is illustrated in FIG. 3, which comprises a pair of crystals 106, 106', each crystal having a photodetector (such as a MAPD) 108, 108' at a distal end. A triangular reflector 110 is disposed between the two crystals 106, 106', such that the signals from the MAPDs 108, 108' resulting from gamma photon interactions within the crystal pair will depend on the location of the interaction within the crystal pair.

Referring to FIG. 2, the detector modules 100A and 100B may represent any two detector modules that are within the relevant field of view in a PET scanner. A source of gamma photons 104 (e.g., from the object under test) between the two detector modules 100A, 100B, for example annihilation events as discussed above, may produce a coincident detection event in the modules. In the present application a "coincident" detection event refers to a detection event in two modules that are close enough in time to be considered coincident for purposes of PET. For example, detection events in two detector modules 100A, 100B that are within a relevant field of view may be considered coincident if they occur within a ten nanosecond period. The actual time span threshold will depend on the particular apparatus and application. Several factors may contribute to the gamma photons in an annihilation event having slightly differing detection times, including the particular location of the annihilation event within the scanner, finite timing resolution of the detector, etc.

An exemplary method and apparatus for data acquisition in PET systems is disclosed in copending U.S. Ser. No. 12/264, 093, published on Sep. 10, 2009, in U.S. Patent Application Publication No. 2009/0224158, which is hereby incorporated by reference in its entirety.

As PET systems become more complex and of larger scale, the massive amounts of data generated by the photodetector arrays used in the systems creates both hardware and software problems during processing. There remains a great need for continued improvement in the cost, efficiency, and accuracy of PET systems, as well as the reduction in complexity and amount of data that must be handled by a software-based computer system.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

In one aspect, an application specific integrated circuit (ASIC) is provided that is useful in a positron emission tomography (PET) system to transfer and process analog signals between a two-dimensional array of photodetectors and a digital processing board; said array of photodetectors comprising rows and columns of photodetectors arranged in a grid, with each photodetector in the array having a common bias voltage; and said ASIC being configured to perform the following functions:

I. sum single-ended analog signals from the array of photodetectors in row, column, and diagonal operations;

II. provide bandwidth amplification of a bias signal from the common bias voltage, said bias signal being useful as a common timing signal for the photodetectors in the array;

III. provide bandwidth amplification for single-ended signals from each photodetector in the array;

IV. produce a total summed signal from the signals from the array;

V. provide a gain adjustment of up to +/−30% for each photodetector prior to summing the signals;

VI. provide bias voltage adjustment for each photodetector in the array;

VII. provide differential signal outputs compatible with analog-to-digital converters on the digital processing board; and     VIII. provide individual addressing of a single photodetector in the array with all other photodetectors excluded.

In another aspect, a method for reducing the number of data signals between an analog photodetector array and a digital processing board in a positron emission tomography (PET) system is provided, comprising the steps of:

(a) providing an application specific integrated circuit (ASIC) to transfer and process analog signals between a two-dimensional array of photodetectors and a digital processing board; said array of photodetectors comprising a square grid of N by N photodetectors; with each photodetector in the array having a common bias voltage; said ASIC being configured to perform the following functions:

I. sum single-ended analog signals from the array of photodetectors in row, column, and diagonal operations in a summing array;

II. provide bandwidth amplification of a bias signal from the common bias voltage, said bias signal being useful as a common timing signal for the photodetectors in the array;

III. provide bandwidth amplification for single-ended signals from each photodetector in the array;

IV. produce a total summed signal from the signals from the array;

V. provide a gain adjustment of up to +/−30% for each photodetector prior to summing the signals;

VI. provide bias voltage adjustment for each photodetector in the array;

VII. provide differential signal outputs compatible with analog-to-digital converters on the digital processing board; and     VIII. provide individual addressing of a single photodetector in the array with all other photodetectors excluded;

(b) routing up to $N^2$ single-ended analog signals from the array of photodetectors into a summing array in the ASIC for a single time increment;

(c) summing the plural number of single-ended analog signals in the summing array using row, column, and diagonal operations to produce between 3N and 4N output signals; and (d) outputting from the ASIC a plural number of differential output analog signals; wherein the plural number of single-ended analog signals input into the ASIC is larger than the plural number of differential-output analog signals.

In another aspect, a data acquisition system is provided for a positron emission tomography scanner having a plurality of detector modules, each detector module having an array of photodetectors associated with corresponding scintillation crystals, the data acquisition system comprising:

(a) for each detector module, a board set including: (i) a detector adaptor board that supplies voltage control to the associated array of photodetectors and receives single-ended analog signals from the associated array of photodetectors, and further comprises means for converting the received single-ended signals to differential pairs; and (ii) a digitizing board that receives and digitizes the differential pair signals from the detector adaptor board and produces an event strobe signal in response to the received differential pair signals;

(b) a master board that receives the event strobe signals from the board sets from each detector module and preliminarily identifies coincident events based on the timing of the received event strobe signals and the location of the detector modules associated with the received event strobe signals;

(c) a master clock board that provides a master clock signal to the board sets;

wherein the master board further comprises means for sending an event_OK signal to the detector modules associated with the identified coincident events, and the digitizing boards further comprise means for responding to the event_OK signal by packaging the digitized differential pair signals associated with the event_OK signal with time stamp data and transmitting the packaged data to an image processing apparatus.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION

Improved processing electronic hardware components are disclosed that facilitate the efficient processing of PET data, while enhancing accuracy and compatibility of PET systems with other analytical methods (e.g., MRI).

The PET system electronics address the basic function of digitizing signals from a PET photodetector. As will be described in further detail below, the system electronics include a plurality of board sets, each set including a photodetector module (e.g., a PMT or MAPD array), a detector adaptor board, and a digital processing board. The plurality of board sets are controlled by a local master board. The plurality of board sets detect photons from the object under test and the resulting detection signals are communicated through the board set and local master board to a computer for PET image construction.

Each board set is configured to digitize the analog signals from the photodetector array, as well as to control the voltage required by the array to operate.

The boards communicate to notify the local master board when an event has occurred ("event strobe"). The local master board then determines when two detectors have events within a user-definable course timing window (e.g., 40 ns) and geometric constraints on the angular separation of each photodetector are satisfied, and communicate the coincident detection event to the system ("event_ok signal"). When an event_ok signal is received by a board that has sent out an event strobe, the board then packages the event data into an event data packet for transmission to the local master board and computer for data processing and image construction.

The electronic hardware of the provided system will now be described in further detail with reference to FIGS. 4-10. Note that arrows used in the diagrams of the figures indicate electrical communication between components. A single-ended arrow indicates one-way communication and a double-ended arrow indicates two-way communication.

It will be appreciated that specific representative embodiments are described below, but these embodiments are meant to be illustrative of the invention and not limiting.

Figure 4:
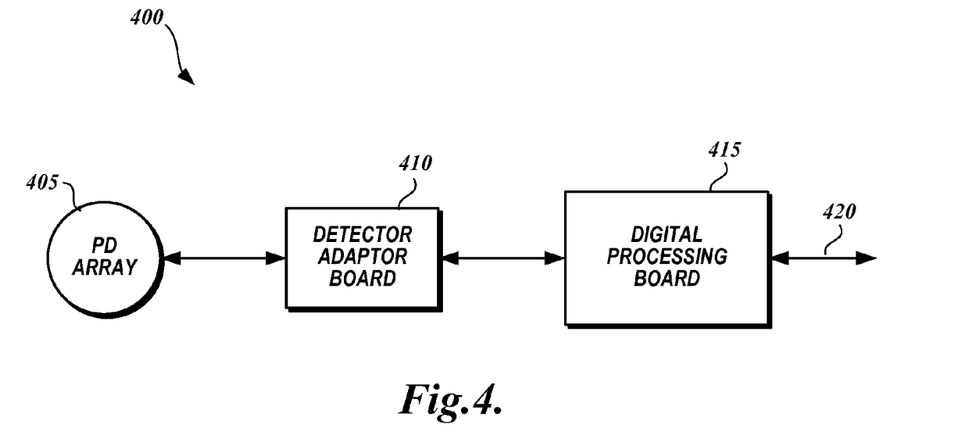
FIG. 4 shows schematically a data acquisition system useful in the present invention.

Referring to FIG. 4, a basic PET data acquisition system 400 (also referred to herein as a "board set") in accordance with the present invention is illustrated. The basic system 400 includes a photodetector array 405. The array 405 is in electronic communication with a detector adaptor board 410, which is in turn in electronic communication with a digital processing board 415. The digital processing board 415 is in electronic communication with a computer having software provided thereon for image construction and system control of the PET systems described herein. Optionally, as will be discussed in more detail below, the digital processing board 415 communicates its data to a local master 815 (FIG. 8) and a scanner master 900 (FIG. 9) prior to receipt of the data at the computer.

The basic processing system 400 can be integrated into a single monolithic board configuration, wherein the photodetector array 405, the detector adaptor board 410, and the digital processing board 415 are essentially mounted on a single substrate, or substantially adjacent to each other. Alternatively, the analog and digital components can be separated (e.g., the analog photodetector array 405 and detector adaptor board 410 can be separated from the digital processing board 415) so as to remove the noise-generating digital elements from an environment sensitive to such disturbances.

For example, for a PET system to be integrated with an MRI system, the digital processing can be removed from the zone of the bore of the MRI so as to eliminate the effects of RF noise on the sensitive MRI field. In this example, the digital processing board 415 would be connected by a cable spanning a distance large enough to remove all RF noise from the MRI system.

Situating the board set 400 in relation to the PET system illustrated in FIG. 1, the ADC 97 of FIG. 1 is a component of the digital processing board 415 and typically immediately accepts the analog signals output by the detector adaptor board 410. The FPGA 98 is also a component on the digital processing board 415. The low-pass filter 96 is an optional component on the detector adaptor board 410 provided herein.

The photodetector array 405 can be any array known to those of skill in the art. In one embodiment, the array is a Geiger-mode avalanche photodiode (GM-APD). GM-APDs require individual gain adjustment and short signal paths for each photodetector in the array 405 to provide optimal performance. GM-APDs provide the benefit of being compatible with magnetic fields (e.g., in an MRI bore). Additional benefits include compact photodetector size (allowing fine-pitch arrays) and low bias voltage requirements.

The detector adaptor board 410 provides several functions, including the following:

(a) accept analog signals from the photodetector array 405;
(b) provide local analog pulse filtering and/or amplification;
(c) convert single-ended signals from the photodetector array 405 to differential signal pairs for transmission to the digital processing board 415;
(d) supply the voltage necessary for the photodetector array 405; and
(e) provide local voltage regulation from the system wide voltage supply.

Figure 5:
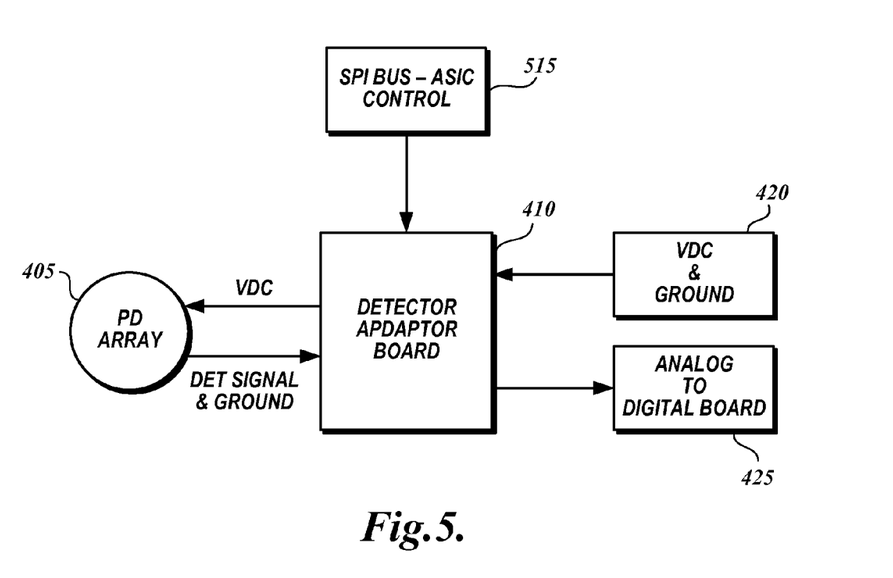
FIG. 5 shows schematically a diagram of a photodetector and detector adaptor board in accordance with the present invention.

FIG. 5 provides a detail schematic illustration of an exemplary detector adaptor board 410 and the related connections thereto. Referring to FIG. 5, the detector adaptor board 410 receives signals from the photodetector array 405 as well as provides power to the array ("VDC"). The detector adaptor board 410 is controlled by a small peripheral instrument (SPI) bus 515 (e.g., connected to an ASIC on the board). The detector adaptor board 410 receives power 420 from upstream electronics (e.g., digital processing board 415). The detector adaptor board 410 additionally provides analog signals 425 (in differential pairs) to the digital processing board 415.

Figure 6A:
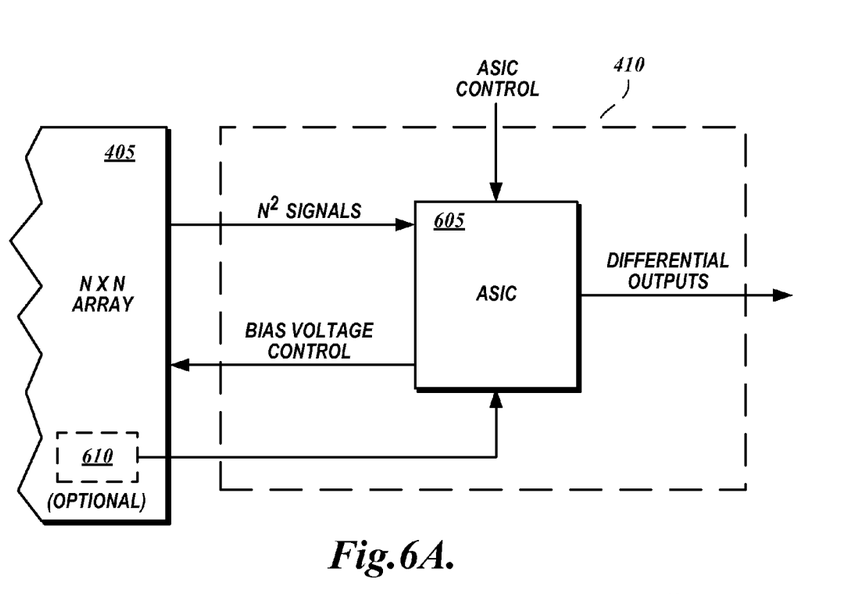
FIG. 6A shows schematically an ASIC integrated into a detector adaptor board in accordance with the present invention.

FIG. 6A is a diagrammatic detail of the detector adaptor board 410, with regard to an ASIC 605 in accordance with the present invention. The ASIC 605 is operatively connected to the photodetector array 405. In the representative embodiment illustrated in FIG. 6A, the photodetector array 405 is an N×N array, wherein N is the number of photodetectors on each side of the grid of the array 405, and thus the number of rows and columns of signals from the array 405. The photodetector array 405 provides $N^2$ signals (one single-ended signal for each photodetector) to the ASIC 605. The ASIC 605 performs summing (e.g., row/column/diagonal) on the input signals from the array 405 and outputs summed differential signals to the digital processing board 415.

The ASIC 605 is controlled either on- or off-board (e.g., through the SPI bus).

The ASIC 605 provides bias voltage control of the individual elements of the array 405.

Optionally, the array 405 includes a temperature sensor 610 that is connected to the ASIC 605 to provide temperature feedback, which allows for the fine-tuning of voltage and/or gain of the elements of the array 405 and/or the measured signals from the array 405.

Figure 6B:
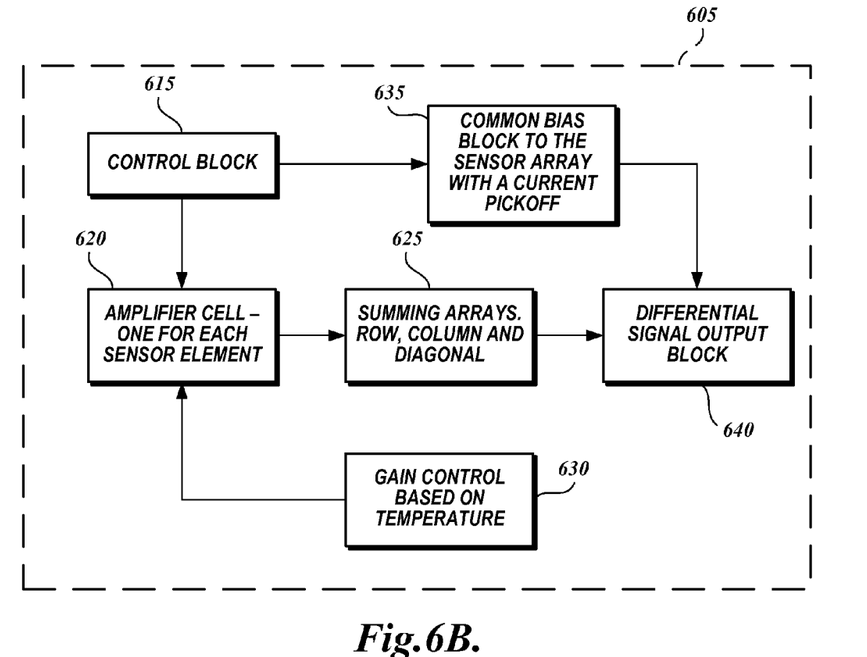
FIG. 6B shows schematically the functions performed by an ASIC in accordance with the present invention.

FIG. 6B is a schematic detail of the functions performed by the ASIC 605. The ASIC includes a control block 615 that provides communication between the ASIC and the photodetector array 405 in the form of a common bias block to the array 605 (for current pickoff) and amplifier cells 620, of which one is provided for each photodetector in the array 405 (e.g., there are $N^2$ amplifier cells 620 in the above-described system). The amplifier cells 620 provide tuning of the raw analog signals from the array 420 prior to entering a summing array 625. A single summing array 625 is illustrated in FIG. 6A, but a plurality of arrays may be utilized. The summing array 625 provided includes the ability to sum the signals from the amplifier cells 620 in row, column, and diagonal functions (e.g., a row of sensors in the array 405 is summed in a row-summing function).

As illustrated in FIG. 6A, an optional temperature sensor 610 can be integrated into the PET system. In FIG. 6B, the output from the temperature sensor 610 is used in the ASIC 605 to adjust the gain of each amplifier cell 620. Depending on the type of photodetector (e.g., MAPD or PMT) used in the array 405, the response of the photodetectors will have a particular temperature dependence, which can be regulated using gain control 630.

The common bias block to the sensor array with a current pickoff 635 enables the ASIC 605 to identify the occurrence of a photodetector event and communicate the event occurrence to the other components of the system for processing. This approach generates a pulse based on the current detected in the common anode bias supply voltage when one or more of the photodetectors (e.g., GM-APD) in the array 405 produces a signal. Thus, a single, fast signal can be generated for any combination of events in the photodetector array for the purpose of coincidence timing.

The common bias block 635 and the summing array 625 each communicate with the differential signal output block 640 for conversion of the relevant data into differential signals for improved signal stability during transport to the digital processing board 415.

The ASIC 605 provides several benefits to the provided PET system, including the ability to very efficiently and compactly (i.e., board-space wise) convert the large amount of data produced by the N×N array 405 into compact summed signals, thus saving large amounts of data from being transported and processed further on in the PET system. For example, an N×N array will produce $N^2$ signals, and row/column summing will reduce this amount of data to 2N. The further use of diagonal summing will increase the amount of data from 2N to 3N or 4N depending on how the diagonal summing is implemented (e.g., summing on one or two diagonals).

An improvement in speed is also realized by having these functions hard-wired in an ASIC (as opposed to software-based implementation) that is in close proximity to the array 405. Particularly, long (e.g., greater than one inch) distances between the array 405 and the ASIC degrade the timing of the entire PET system such that coincidence timing is compromised. Additionally, skew times between photodetectors are reduced by reducing the distance between the array 405 and signal processing in the ASIC.

The use of diagonal summing in the ASIC provides additional benefits when dMiCE detectors are used in the array 405 because simple row/column summing of the signals of the array 405 may not provide sufficient information to properly interpret and identify the size, location, and timing of a detection event. The addition of diagonal summing provides another segment of data that greatly increases the ability of the PET system to properly detect and identify incident photons. Particularly, to find the point of first interaction (i.e., of a detected photon in the array), the crystals that produced the light and the amount of light must be determined. Any multiplexing scheme (e.g., row/column/diagonal summing) must allow for total recovery of the data from each individual crystal photodetector of the array 405. In some instances, crystals in immediate proximity to each other can all be involved in a single detection event, and row/column data alone will not allow for complete recovery of the signals generated from the event. The addition of diagonal summing remedies this issue.

The ASIC provided performs several functions when incorporated into a PET system. These functions include any combination of the following:
(a) provide wide bandwidth (300 MHz amplification of single-ended signals from each photodetector array element);
(b) support row/column/diagonal summing of the array elements;
(c) provide a total summed signal from the common bias voltage;

(d) provide gain adjustment (up to +/−30%) for each element of the array prior to connection to the summing network;
(e) provide limited bias voltage adjustment for each element of the array;
(f) provide differential outputs compatible with the digital processing board;
(g) provide a mechanism to allow selection of each element in the array (one at a time, all others disconnected) to be connected to the summing network;
(h) control ASIC functions via a serial command interface (read/write);
(i) provide wide bandwidth amplification (300 MHz or greater) of a bias signal from the common bias voltage (e.g., the common timing signal); and
(j) provide feedback from a temperature sensor mounted on the photodetector array so as to fine tune control of the gain and/or bias voltage of each element of the array.

Figure 7:
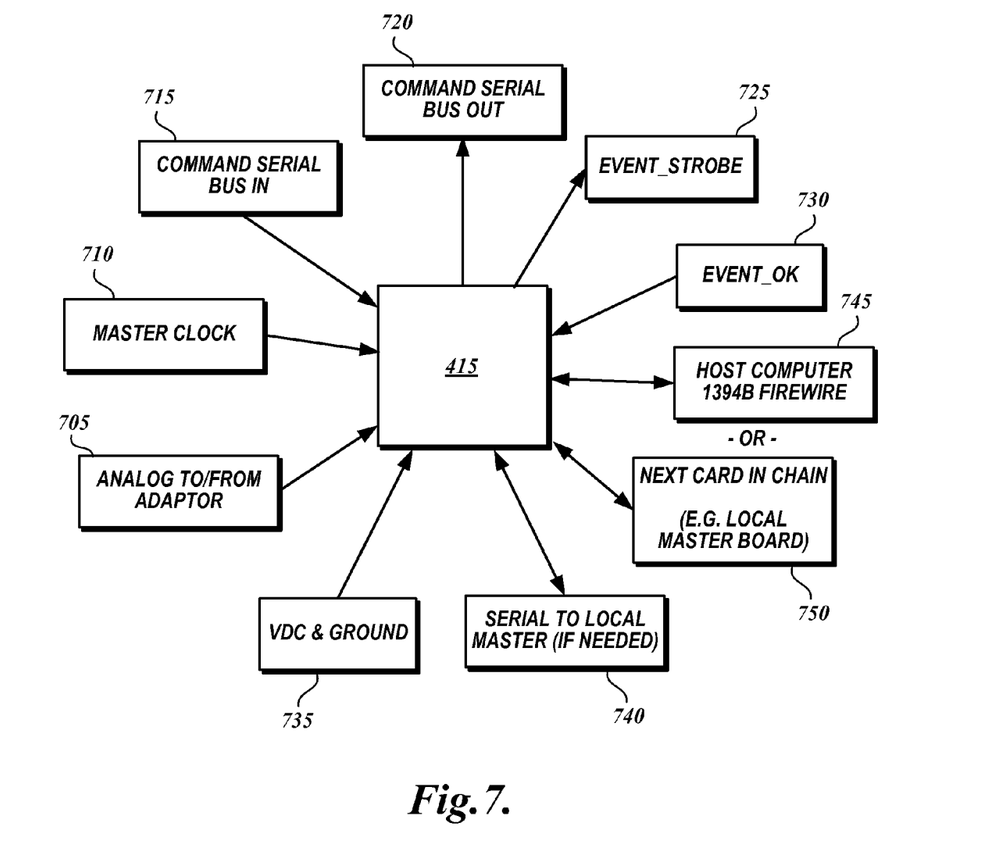
FIG. 7 shows schematically a digital processing board in accordance with the present invention.

Referring to FIG. 7, the digital processing board 415 is schematically detailed. The digital processing board receives analog signals 705 from the detector adaptor board 410 and converts the analog signals to digital signals. Additionally illustrated are the master clock signal 710, command serial bus in 715, command serial bus out 720, event_strobe out 725, event_ok in 730, voltage in 735, and an optional serial interface 740 to a local master board 815 (FIG. 8).

The digital processing board 415 provided herein is a highly customizable and reconfigurable element of the PET electronics system. The digital processing board 415 can act as a standalone digital processing element, providing a bridge between the analog photodetector array 405 signals and a host computer, or the digital processing board 415 can be a hub for data in a larger system wherein several modules are combined, each comprising a photodetector array 405, a detector adaptor board 410, and a digital processing board 415. For example, the digital processing board 415 can be linked to a host computer 745 or linked 750 to a local master board 815 to create a "star" topology of several photodetector module nodes, as discussed below in reference to FIG. 8. Such a star topology is useful for combining the data from photodetector arrays disposed on opposite sides of an object under test so as to receive both photons from an annihilation event.

Figure 8:
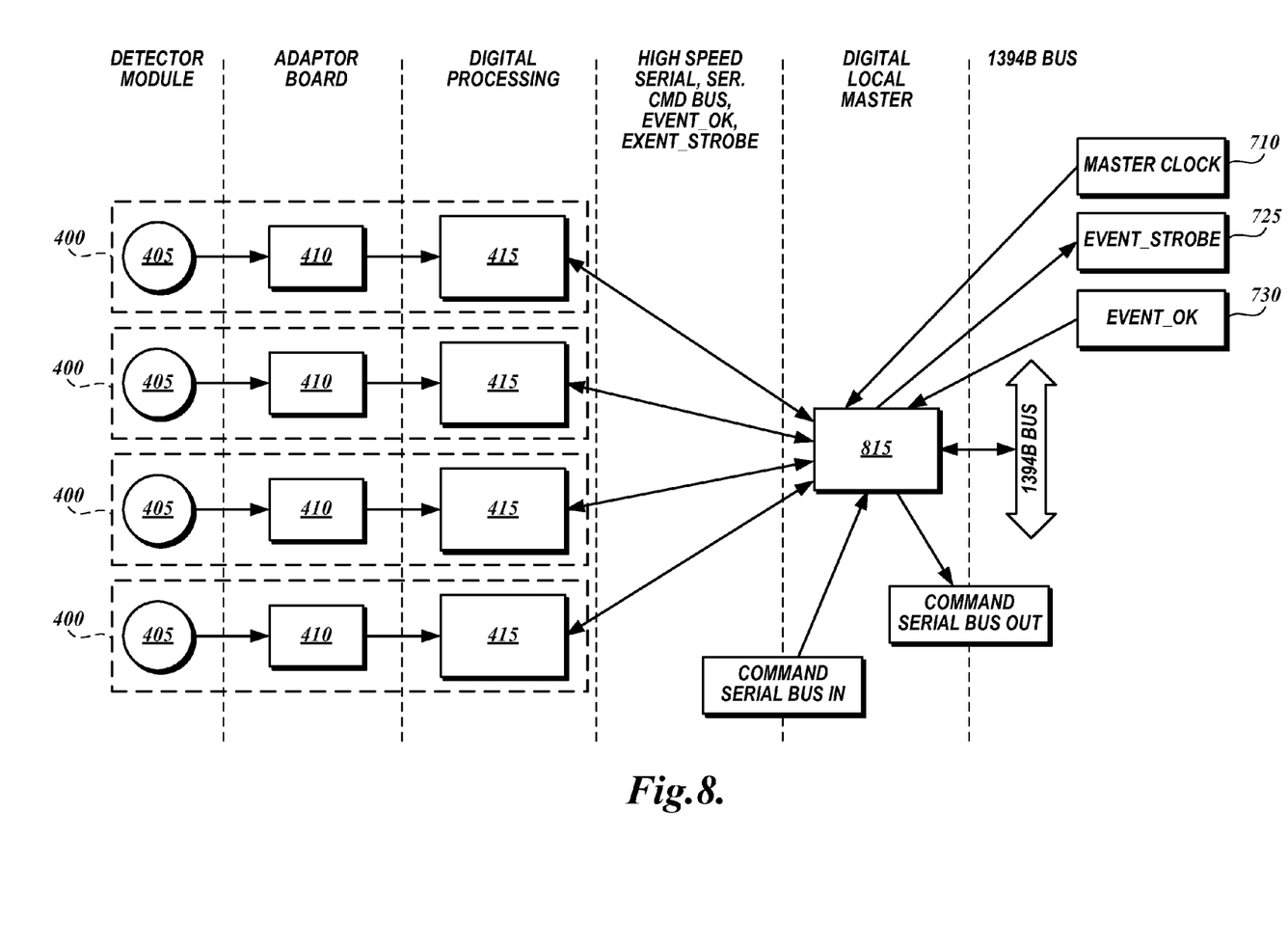
FIG. 8 shows schematically a system for digitally processing photodetector signals in accordance with the present invention.

Referring to the star topology illustrated in FIG. 8, a plurality of digital acquisition systems 400 (four shown) are routed into the local master digital processing board 815, which has the same hardware as the digital processing board 415, but is configured via input commands (e.g., on an FPGA) to act as an aggregator of signals from the local digital processing boards 415. The local master board 815 then communicates with the host computer via a scanner master 900 (FIG. 9).

FIG. 8 includes columns describing the functions of various aspects of the system demarcated by dashed lines.

Figure 9:
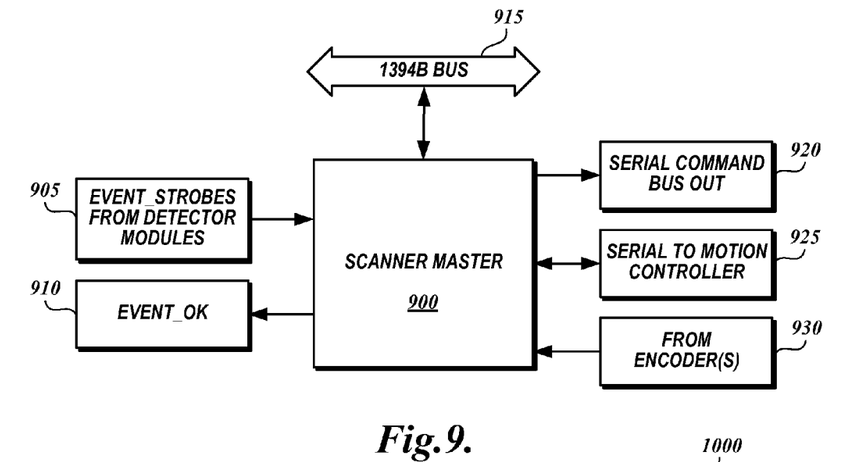
FIG. 9 shows schematically a detailed diagram of an electronic component useful for controlling several photodetector modules in accordance with the present invention.

The scanner master 900 is illustrated in more detail in FIG. 9, wherein the flow of signals is more clearly depicted. The scanner master 900 intakes event_strobes from the detector module 905 (e.g., FIG. 4) and returns event_ok signals 910 to the downstream components. The scanner master board 900 additionally communicates with the host computer (e.g., via the 1394b bus 915) and provides serial command bus out signals 920, two-way communication with a motion controller 925 (for scanner applications that require mechanical motion of the photodetector array and/or imaging table), and data from encoder(s) 930 (used to monitor any motion) is received and processed on the scanner master 900.

The scanner master 900 can be attached to one, or several, local master boards 815 and the event_strobe signals from each are processed on the scanner master 900. The scanner master 900 then generates an event_ok signal if two event_strobes are within a course-timing window and the two event_strobes are from detectors in an allowed geometric configuration.

In an exemplary embodiment of the digital adaptor board 415, the local master board 815, and the scanner master 900, all three boards are similar in electronic components. In this embodiment, the boards are each driven by an FPGA, which is loaded with a specific instruction set based on the use of the board (e.g., if the board is to be used a scanner master 900, the FPGA will be instructed to perform the event_ok and event_strobe functions, as well as communicate with adjacent components, etc.).

Figure 10:
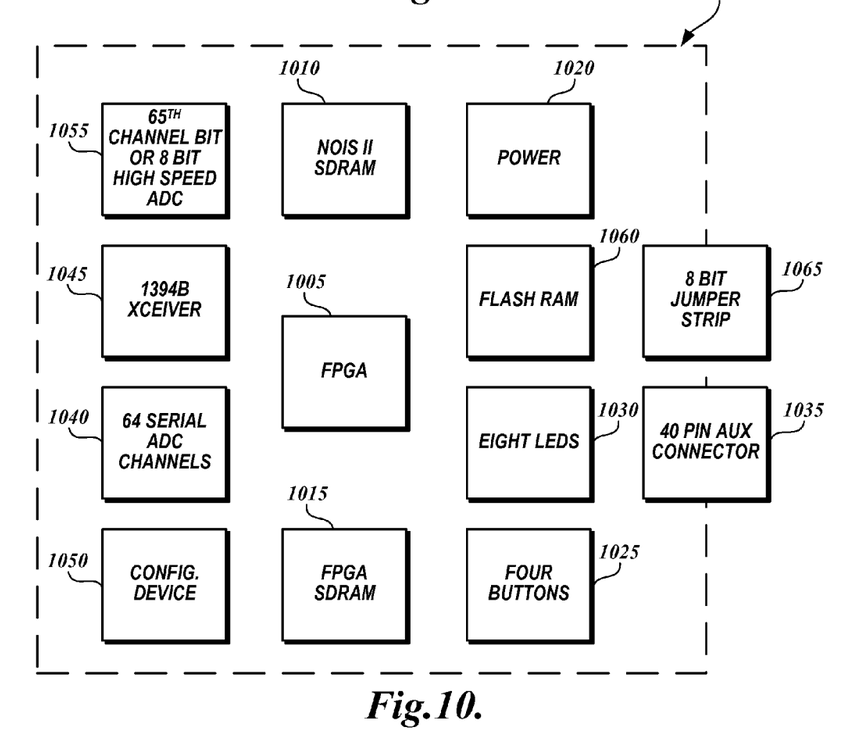
FIG. 10 shows schematically a digital processing board in an exemplary embodiment of the present invention.

FIG. 10 is a diagrammatic illustration of an exemplary board configuration 1000 of components useful within the digital processing board 415 according to the embodiments disclosed herein. The field-programmable gate array (FPGA) 1005 is the central processing component, which is controlled by the software language NOIS II (via SDRAM) 1010 and FPGA code from a second SDRAM 1015 (e.g., algorithms for determining scintillation-event positioning). The board 1000 includes power 1020, buttons 1025 (for local diagnostics), LEDs 1030 (for indicator functions), and input and output connections 1035. In the exemplary board 1000 of FIG. 10, 64 digitally converted channels from the photodetector array 1040 are illustrated, as well as a Firewire 1394B transceiver 1045, a configuration device 1050, and a 65th channel 1055 for optional functions, such as temperature input from the photodetector array. The flash RAM 1060 supports the FPGA 1005.

It will be appreciated that while Firewire is used in the exemplary embodiments described herein (e.g., Firewire 1394B transceiver 1045), other communication standards (e.g., Ethernet) are suitable, with each communication standard requiring its own transceiver and FPGA code segments.

The 8-bit jumper strip 1065 allows encoding a unique identifier for each board. The identifier is included in the data stream from each board to allow image reconstruction software to correctly place the detectors associated with each board in the coordinate system of the scanner.

In another aspect, a data acquisition system for a PET scanner is provided. The system may include the components described above (e.g., ASIC 605, photodetector array 405, and detector adaptor board 410). The system includes a plurality of digital acquisition systems 400 ("detector modules") having photodetector arrays 405 ("arrays of photodetectors") associated with corresponding scintillation crystals, the data acquisition system comprising:

(a) for each system 400, a board set including: (i) a detector adaptor board 410 that supplies voltage control to the associated photodetector array 405 and receives analog signals from the associated photodetector array 405, and further comprises means for converting the received signals to differential pairs (e.g., ASIC 605); and (ii) a digitizing board (e.g., digital processing board 415) that receives and digitizes the differential pair signals 425 from the detector adaptor board 410, and produces an event strobe signal 725 in response to the received differential pair signals 425;

(b) a master board 825 that receives the event strobe signals 725 from the board sets from each detector module 805 and preliminarily identifies coincident events based on the timing of the received event strobe signals 725 and the location of the detector modules associated with the received event strobe signals 725;

(c) a master clock board that provides a master clock signal to the board sets;

wherein the master board further comprises means for sending an event_OK signal 730 to the detector modules associated with the identified coincident events, and the digitizing boards further comprise means for responding to the event_OK 730 signal by packaging the digitized differential pair signals associated with the event_OK 730 signal with time stamp data and transmitting the packaged data to an image processing apparatus (e.g., a computer).

In one embodiment of the data acquisition system, the analog components (e.g., photodetector array 405 and detector adaptor board 410) and digital components (e.g., digital processing board 415 and computer) are separated by a distance sufficient to eliminate RF signal interference generated by the digital components at the analog components. As described above, the separation of digital and analog components facilitates the use of PET systems with RF-noise-sensitive modalities, such as MRI. The digital and analog components may be separated by several feet of communication line (e.g., electrical wire), or the shielding of noise can be accomplished by providing an electronic and/or physical barrier between the analog and digital components (e.g., a wall with only the communication lines penetrating the wall). A combination of distance and barriers is also contemplated.

In another aspect, similar to the embodiments provided above, a method for reducing the number of data signals between an analog photodetector array and a digital processing board in a positron emission tomography (PET) system is provided, comprising the steps of:

(a) providing an application specific integrated circuit (ASIC) to transfer and process analog signals between a two-dimensional array of photodetectors and a digital processing board; said array of photodetectors comprising a square grid of N by N photodetectors; with each photodetector in the array having a common bias voltage; said ASIC being configured to perform the following functions:

I. sum single-ended analog signals from the array of photodetectors in row, column, and diagonal operations in a summing array;

II. provide bandwidth amplification of a bias signal from the common bias voltage, said bias signal being useful as a common timing signal for the photodetectors in the array;

III. provide bandwidth amplification for single-ended signals from each photodetector in the array;

IV. produce a total summed signal from the signals from the array;

V. provide a gain adjustment of up to +/−30% for each photodetector prior to summing the signals;

VI. provide bias voltage adjustment for each photodetector in the array;

VII. provide differential signal outputs compatible with analog-to-digital converters on the digital processing board; and VIII. provide individual addressing of a single photodetector in the array with all other photodetectors excluded;

(b) routing up to $N^2$ single-ended analog signals from the array of photodetectors into a summing array in the ASIC for a single time increment;

(c) summing the plural number of single-ended analog signals in the summing array using row, column, and diagonal operations to produce between 3N and 4N output signals; and (d) outputting from the ASIC a plural number of differential output analog signals; wherein the plural number of single-ended analog signals input into the ASIC is larger than the plural number of differential-output analog signals.

Embodiments of this method include similar structures (ASIC) and processing steps as described in previous embodiments.

While illustrative embodiments have been illustrated and described, it will be appreciated that various changes can be made therein without departing from the spirit and scope of the invention.

The invention claimed is:

1. An application specific integrated circuit (ASIC) useful in a positron emission tomography (PET) system to transfer and process analog signals between a two-dimensional array of photodetectors and a digital processing board;
said array of photodetectors comprising rows and columns of photodetectors arranged in a grid, with each photodetector in the array having a common bias voltage; and
said ASIC being configured to perform the following functions:

(I) sum single-ended analog signals from the array of photodetectors in row, column, and diagonal operations;

(II) provide bandwidth amplification of a bias signal from the common bias voltage, said bias signal being useful as a common timing signal for the photodetectors in the array;

(III) provide bandwidth amplification for single-ended signals from each photodetector in the array;

(IV) produce a total summed signal from the signals from the array;

(V) provide a gain adjustment of up to +/−30% for each photodetector prior to summing the signals;

(VI) provide bias voltage adjustment for each photodetector in the array;

(VII) provide differential signal outputs compatible with analog-to-digital converters on the digital processing board; and (VIII) provide individual addressing of a single photodetector in the array with all other photodetectors excluded.

2. The ASIC of claim 1, further configured to provide gain control of a photodetector of the array according to an input signal from a temperature sensor adjacent the array.

3. The ASIC of claim 1, wherein the function of producing a total summed signal from the signal array further comprises producing a slow sum of each photodetector of the array with a bandwidth of 300 MHz or less.

4. The ASIC of claim 1, wherein the function of producing a total summed signal from the signal array is accomplished by detecting a common bias voltage pickoff signal.

5. The ASIC of claim 1, wherein the photodetector array is a Geiger-mode avalanche photodiode array.

6. The ASIC of claim 1, wherein the photodetector array is optically coupled to a continuous miniature crystalline element scintillator.

7. The ASIC of claim 1, wherein the photodetector array is optically coupled to a discrete miniature crystalline element scintillator.

8. The ASIC of claim 1, wherein the function of summing signals from the array of photodetectors in row, column, and diagonal operations is accomplished using a plurality of summing arrays, wherein each photodetector in the array is linked to each of the plurality of summing arrays.

9. A data acquisition system for a positron emission tomography scanner having a plurality of detector modules, each detector module having an array of photodetectors associated with corresponding scintillation crystals, the data acquisition system comprising:

(a) for each detector module, a board set including: (i) a detector adaptor board that supplies voltage control to the associated array of photodetectors and receives single-ended analog signals from the associated array of photodetectors, and further comprises means for converting the received single-ended signals to differential pairs; and (ii) a digitizing board that receives and digitizes the differential pair signals from the detector adaptor board and produces an event strobe signal in response to the received differential pair signals;

(b) a master board that receives the event strobe signals from the board sets from each detector module and preliminarily identifies coincident events based on the timing of the received event strobe signals and the location of the detector modules associated with the received event strobe signals;

(c) a master clock board that provides a master clock signal to the board sets;

wherein the master board further comprises means for sending an event_OK signal to the detector modules associated with the identified coincident events, and the digitizing boards further comprise means for responding to the event_OK signal by packaging the digitized differential pair signals associated with the event_OK signal with time stamp data and transmitting the packaged data to an image processing apparatus.

10. The data acquisition system of claim 9, wherein the detector adaptor board further comprises an application specific integrated circuit (ASIC) configured to sum the single-ended analog signals from the array of photodetectors in row, column, and diagonal operations.

11. The data acquisition system of claim 9, wherein analog components and digital components are separated by at least one of distance, electrical shielding, and physical shielding, sufficient to eliminate RF signal interference generated by the digital components at the analog components.

12. The data acquisition system of claim 11, wherein the analog components are incorporated within a bore of a magnetic resonance imaging system and the digital components are outside of the bore, and wherein the RF signal interference generated by the digital components does not adversely affect the performance of the MRI system.

13. The data acquisition system of claim 9, wherein the digitizing board, the master board, and the master clock board all have the same electronic components.

14. A method for reducing the number of data signals between an analog photodetector array and a digital processing board in a positron emission tomography (PET) system, comprising the steps of:

(a) providing an application specific integrated circuit (ASIC) to transfer and process analog signals between a two-dimensional array of photodetectors and a digital processing board; said array of photodetectors comprising a square grid of N by N photodetectors; with each photodetector in the array having a common bias voltage; said ASIC being configured to perform the following functions:
  (I) sum single-ended analog signals from the array of photodetectors in row, column, and diagonal operations in a summing array;
  (II) provide bandwidth amplification of a bias signal from the common bias voltage, said bias signal being useful as a common timing signal for the photodetectors in the array;
  (III) provide bandwidth amplification for single-ended signals from each photodetector in the array;
  (IV) produce a total summed signal from the signals from the array;
  (V) provide a gain adjustment of up to +/−30% for each photodetector prior to summing the signals;
  (VI) provide bias voltage adjustment for each photodetector in the array;
  (VII) provide differential signal outputs compatible with analog-to-digital converters on the digital processing board; and
  (VIII) provide individual addressing of a single photodetector in the array with all other photodetectors excluded;

(b) routing up to $N^2$ single-ended analog signals from the array of photodetectors into a summing array in the ASIC for a single time increment;

(c) summing the plural number of single-ended analog signals in the summing array using row, column, and diagonal operations to produce between 3N and 4N output signals; and (d) outputting from the ASIC a plural number of differential output analog signals; wherein the plural number of single-ended analog signals input into the ASIC is larger than the plural number of differential-output analog signals.

15. The method of claim 14, wherein the photodetector array is optically coupled to a continuous miniature crystalline element scintillator.

16. The method of claim 14, wherein the photodetector array is optically coupled to a discrete miniature crystalline element scintillator.

17. The method of claim 14, wherein the function of summing signals from the array of photodetectors in row, column, and diagonal operations is accomplished using a plurality of summing arrays, wherein each photodetector in the array is linked to each of the plurality of summing arrays.

* * * * *